United States Patent [19]
Rubens et al.

[11] Patent Number: 5,324,647
[45] Date of Patent: Jun. 28, 1994

[54] FIBRIN COATED POLYMER SURFACES

[75] Inventors: Fraser D. Rubens, Burlington, Canada; Paul D. Bishop, Fall City, Wash.

[73] Assignees: McMaster University, Hamilton, Canada; ZymoGenetics, Inc., Seattle, Wash.

[21] Appl. No.: 121,327

[22] Filed: Sep. 14, 1993

Related U.S. Application Data

[62] Division of Ser. No. 872,483, Apr. 23, 1992, Pat. No. 5,272,074.

[51] Int. Cl.$^5$ .................. C12N 11/08; A61K 37/547; A01N 1/02
[52] U.S. Cl. ................. 435/180; 424/44.64; 427/2; 436/8; 600/36
[58] Field of Search ................. 424/94.64; 435/1, 180; 436/8; 600/36; 427/2

[56] References Cited

U.S. PATENT DOCUMENTS

| | | | |
|---|---|---|---|
| 4,167,045 | 9/1979 | Sawyer | 427/2 |
| 4,273,873 | 6/1981 | Sugitachi et al. | 435/180 |
| 4,534,069 | 8/1985 | Kelman | 623/6 |
| 4,627,879 | 12/1986 | Rose et al. | 106/124 |
| 5,131,907 | 7/1992 | Williams et al. | 600/36 |
| 5,171,261 | 12/1992 | Noishiki et al. | 623/1 |
| 5,230,693 | 7/1993 | Williams et al. | 600/36 |
| 5,266,476 | 11/1993 | Sussman et al. | 435/240.23 |

FOREIGN PATENT DOCUMENTS

| | | |
|---|---|---|
| 290462 | 11/1988 | European Pat. Off. |
| 366564 | 5/1990 | European Pat. Off. |
| 91/16009 | 10/1991 | PCT Int'l Appl. |

OTHER PUBLICATIONS

Noishiki, Y., et al., "The Journal of Thoracic and Cardiovascular Surgery," vol. 104(3), Sep. 1992, p. 5A, 770-778.
Leseche, G., et al., "Surgery", vol. 105(1), Jan. 1989, pp. 36-45.
Zilla, P., et al., "Journal of Vascular Surgery," vol. 6(6), Dec. 1987, p. 5A, 535-541.
Fasol, R., et al., "Vascular Surgery," vol. 25(1), Jan.-/Feb. 1991, pp. 64-71.
Tizian, C., et al., "Thorac. Cardiovasc. Surgeon," vol. 28, 1980, pp. 273-276.
Anderson et al., *Surg.* 101:577-586, 1987.
Voegel et al., *Colloids and Surfaces* 25: 139-144, 1987.
Schwartz et al., *J. Biol. Chem.* 248: 1395-1407, 1973.
Giusti et al., *Life Support Syst.*, 3(Suppl. 1, Proc.-Eur. Soc. Artif. Organs) 476-480, 1986.
Obara et al., *FEBS Lett.* 213: 261-264, 1987.
Yamada, *Cur. Opin. Cell. Biol.* 1: 956-963, 1989.
Mosquera et al., *Br. J. Surg.* 78: 656-660, 1991.
Budd et al., *Br. J. Surg.* 76: 1259-1261, 1989.
Rupnick et al., *J. Vasc. Surg.* 9: 788-795, 1989.
Kaehler et al., *J. Vasc. Surg.* 9: 535-541, 1989.
Lindblad et al., *Acta Chirurg. Scand.* 152: 653-656, 1986.
Mazzucotelli et al., *Int. J. Artif. Organs* 14: 482-490, 1991.
Kent et al., *Trans. Am. Soc. Artif. Intern. Organs* 34: 578-580, 1988.

Primary Examiner—Douglas W. Robinson
Assistant Examiner—Kristin Larson
Attorney, Agent, or Firm—Gary E. Parker

[57] ABSTRACT

Surfaces of polymeric materials are coated with a layer of thermally denatured fibrinogen. The fibrinogen may be treated with thrombin to produce fibrin, and additional fibrinogen and factor XIII added to produce a cross-linked fibrin coating. The resulting coated surface is stable, anti-thrombotic and resistant to platelet adhesion. Polymeric materials coated in this way are useful in constructing vascular grafts and prosthetic devices, and provide test systems useful in the study of thrombogenesis.

10 Claims, 7 Drawing Sheets

FIBRIN COATED POLYMER SURFACES

This is a divisional application of co-pending application Ser. No. 07/872,483, filed Apr. 23, 1992, now U.S. Pat. No. 5,272,074.

BACKGROUND OF THE INVENTION

Occlusive arterial disease is commonly treated by bypassing the occluded vessel. The most successful treatment is achieved through the use of autogenous vein grafts. However, when vein is not available, synthetic grafts made of such materials as expanded polytetrafluoroethylene or polyethyleneterephthalate are substituted.

The surgical application or small caliber synthetic vascular grafts for medium or small vessel bypass is limited by frequent graft occlusion due to the thrombogenic nature of currently available graft materials. In small vessel grafts, blood flow is reduced and there is a rapid adsorption and accumulation of blood proteins on the graft surface. Shortly after implantation in a patient, the luminal aspect of a prosthetic vascular graft heals by the formation of a surface of fibrin referred to as the pseudointima. Thrombin binds to this fibrin pseudointima, where it can contribute to platelet activation and the formation of platelet rich thrombi. Bound thrombin may also contribute to further fibrin accretion that in turn leads to distal embolism.

The seeding of vascular grafts with endothelial cells has been proposed as a solution to the problem of thrombogenicity (reviewed by Mosquera and Goldman, *Br. J. Surg.* 78: 656–660, 1991). Although endothelial seeding of grafts has shown beneficial results in experimental settings, the technology has not progessed to the point that seeded grafts suitable for routine use can be produced.

There is a clear need in the art for biologically compatible, synthetic materials having reduced thrombogenicity. Such materials should be resistant to the deposition of blood proteins and to platelet adherence. These materials would be useful as vascular grafts, synthetic heart valves, artificial organs and in any prosthetic application where the material will be exposed to blood and a potential for thrombogenesis exists. The present invention provides such materials and methods for preparing the materials. Materials prepared in accordance with the methods of the present invention are also useful as experimental models in the study of thrombogenic and fibrinolytic processes.

DISCLOSURE OF THE INVENTION

The present invention provides methods for coating surfaces of polymeric materials with fibrinogen and fibrin. Within one embodiment, the polymeric material is polyethylene, polyethyleneterephthalate or expanded polytetrafluoroethylene, and may be in the form of a vascular graft.

According to one aspect of the invention, a polymeric material is incubated in a solution of fibrinogen at a temperature of at least 56° C. but less than 100° C., preferably about 70° C., to produce a fibrinogen-coated material. Within one embodiment, the solution contains between 0.5 and 3.0 mg/mL fibrinogen, preferably about 1 mg/mL fibrinogen. Within another embodiment, the fibrinogen is human fibrinogen.

According to a related aspect of the invention, a fibrinogen-coated polymeric material, prepared as disclosed above, is treated with thrombin to produce fibrin monomers. Within one embodiment, this treatment is carried out by exposing the fibrinogen-coated surface to a solution containing about 1 µg/mL thrombin. Within another embodiment, the thrombin-treated surface is exposed to a second solution comprising factor XIII and additional fibrinogen, whereby the additional fibrinogen is converted to fibrin and cross-linked to the fibrin-coated surface. The concentration of factor XIII in the second solution is preferably 0.25–5.0 µg/mL. Within a related embodiment, the second solution further comprises basic fibroblast growth factor, endothelial cell growth factor, $\alpha_2$ macroglobulin, vitronectin, fibronectin, or a cell-binding fragment of fibronectin. Within another embodiment, the second solution comprises endothelial cells. Within a related embodiment, the cross-linked fibrin coated surface is seeded with endothelial cells.

The present invention further provides polymeric materials prepared according to the above-disclosed methods.

These and other aspects of the present invention will become evident upon reference to the following detailed description and the attached drawings.

DETAILED DESCRIPTION OF THE INVENTION

Figure 1:
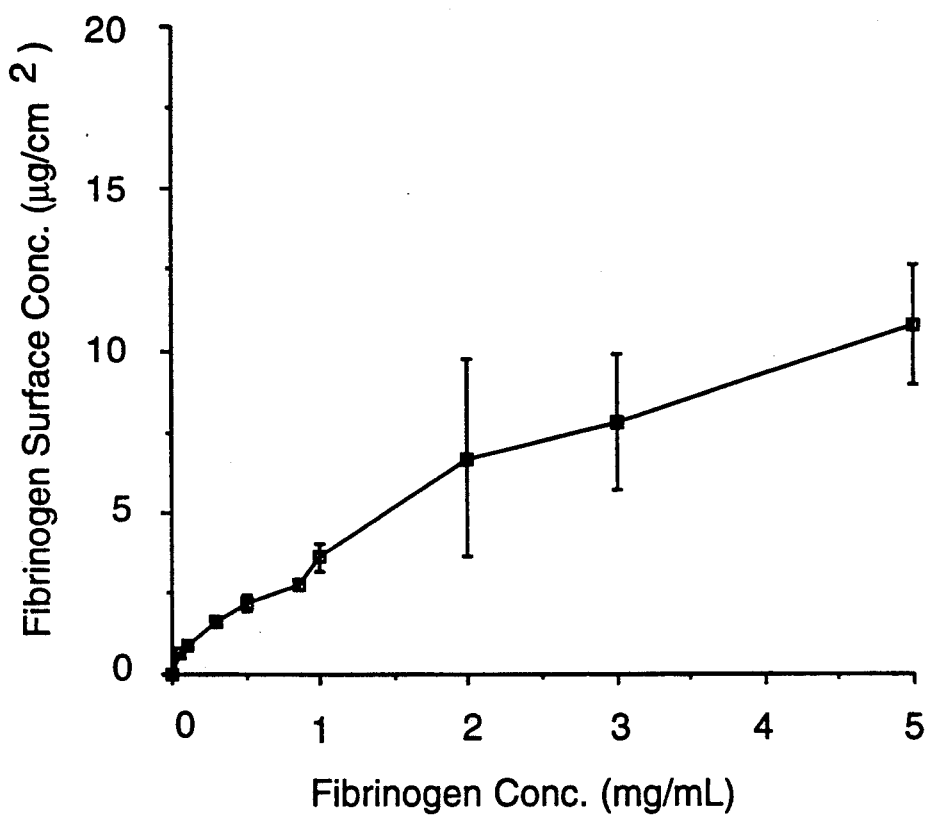
FIG. 1 illustrates the relationship between the concentration of fibrinogen deposited on a surface via thermal denaturation and the concentration of fibrinogen in the starting solution.

The present invention provides methods for coating a surface of a polymeric material such as polyethylene, polyethyleneterephthalate (e.g. Dacron®) or expanded polytetrafluoroethylene (e.g. Gore-Tex®, W. L. Gore, Flagstaff, Ariz.) with fibrinogen. The coated surface may be further treated with thrombin, followed by incubation with additional fibrinogen in the presence of factor XIII. Fibrin-coated surfaces prepared in accordance with the present invention provide substrates for the growth of endothelial cells, prosthetic devices (including vascular grafts) having reduced thrombogenicity, and test systems for the study of thrombogenesis and fibrinolysis.

According to the present invention, a surface of a polymeric material is coated with fibrinogen through a process of heat denaturation. It has been found that the adherence of fibrinogen to polymeric surfaces can be greatly enhanced by thermal denaturation of the fibrinogen at a temperature sufficient to denature the D-domain of fibrinogen but not the E-domain. Thus, heat denaturation is carried out at a temperature of at least 56° C. but less than 100° C. In general, it is preferred to use a temperature of about 70° C., although those skilled in the art will recognize that the actual temperature may be varied within the above-mentioned range to suit the particular polymer used. The temperature will be sufficiently high to heat the entire polymer to at least 56° C. without melting or otherwise damaging the polymer. Such temperature determination is within the level of ordinary skill in the art. In a typical coating procedure, polyethylene tubing is rinsed with methanol to remove any lipid contaminants, followed by a rinse in TBS (0.05M Tris pH 7.4, 0.1M NaCl). The rinsed tubing may then be stored in TBS. The tubing is then drained and filled with a solution of fibrinogen (0.5–3.0 mg/mL) in a pH 6.0–8.0 buffer containing a physiologic concentration of NaCl (e.g. TBS), then placed in an oven at 70° C. for ten to thirty minutes. The tubing is then rinsed with 40 tube volumes of TBS.

Fibrinogen-coated surfaces prepared as described above may be stabilized by treatment with thrombin, factor XIII and additional fibrinogen. It has been found by the inventors that factor XIII stabilizes the deposited fibrin, making it resistant to the high fluid shear rates to which vascular grafts are subjected. The present invention thus provides polymer tubes having a thin, uniform coat of polymerized fibrin which can serve as a reproducible model of neointima on vascular grafts.

To stabilize the fibrinogen coating, a fibrinogen-coated surface, prepared as disclosed above, is treated with α-thrombin. In a typical procedure, a solution of human α-thrombin (0.5–10 µg/mL) in a hypotonic (0.04–0.065M NaCl) pH 6.0–8.0 solution (e.g. 0.025M Tris, 0.05M NaCl, pH 7.4) is applied to the denatured fibrinogen-coated surface at a temperature of about 18° C. to about 37° C. for about 5–10 minutes. The thrombin cleaves fibrinopeptide A from the deposited fibrinogen and converts the fibrinogen to fibrin monomers. Exposure of the resulting fibrin to a solution containing fibrinogen and factor XIII leads to the conversion of the additional fibrinogen to fibrin by thrombin adsorbed to the deposited fibrin layer. Factor XIII then catalyzes the cross-linking of the fibrin, resulting in the formation of a thin, uniform coat of polymerized fibrin. In general, a fibrinogen concentration of about 0.5 to 5.0 mg/mL in a physiologic buffer (pH 6.0–8.0) containing 2 to 10 mM $CaCl_2$, preferably about 2 mM $CaCl_2$, will be used. Factor XIII is included at a preferred concentration of about 0.25 to 20 µg/mL or greater, more preferably about 0.25–1.0 µg/mL. Surfaces prepared in this way provide a reproducible model of neointima on vascular grafts. The surfaces are stable when perfused, under conditions of high wall shear rates, with buffer solutions, cell suspensions and plasma. Surfaces prepared in accordance with the present invention are useful in the study of thrombogenesis and fibrinolysis on vascular grafts.

The thickness of the cross-linked fibrin coating is proportional to the time for which the tubing is exposed to the fibrinogen-factor XIII solution. The relationship between time and coating thickness for any particular surface or set of reaction conditions can be readily established empirically. In a typical procedure, a segment of fibrinogen-coated polymer tubing is filled with a 1 µg/mL solution of human α-thrombin in 0.5× TBS and allowed to stand at about 23° C. for about five minutes. The tubing is then rinsed with 20 tube volumes of 0.5× TBS. The rinsed tubing is then filled with a solution of 1 mg/mL fibrinogen in TBS containing 2 mM $CaCl_2$ and 0.5 µg/mL factor XIII. The mixture is left in the tubing until the desired thickness of cross-linked fibrin is obtained, typically about five minutes. The tubing is then rinsed extensively with TBS. Additional crosslinking can be obtained by further incubation of the rinsed tubing (e.g. 30 minutes-24 hours at 37° C.). Crosslinking of the fibrin is catalyzed by factor XIII bound in the coating. The thrombogenicity of the fibrin-coated polymer surface is reduced significantly by increasing the degree of cross-linking, as platelet adhesion is reduced. These test methods may be used to determine reaction conditions (e.g. time, temperature and protein concentration) for producing different thicknesses of fibrin coatings and different degrees of cross-linking. In some instances it will be desirable to depart from the preferred ranges of conditions disclosed above.

Fibrin-coated polymer surfaces prepared according to the present invention may be seeded with endothelial cells. Endothelial cell seeding of vascular grafts and other surfaces exposed to the blood provides prosthetic materials that are actively antithrombotic and exhibit increased resistance to occlusion. The stability of the fibrin coating makes it an excellent substrate for endothelial cell seeding.

Endothelial cells are obtained by standard procedures from umbilical vein, saphenous vein or other sources. See, for example, Balconi et al., *Med. Biol.* 64: 231–245, 1986; Ryan et al., *Tissue Cell* 17: 171–176, 1985; Budd et al., *Br. J. Surg.* 76: 1259–1261, 1989. Cells can be harvested by mechanical or, preferably, enzymatic methods. Briefly, veins are flushed to remove blood and filled with a collagenase solution to dislodge the endothelial cells. The cells are collected and cultured in a conventional medium. For seeding, the cells are cultured on the fibrin coated surface in the presence of culture medium, generally at about 37° C. in a 5% $CO_2$ atmosphere. Satisfactory attachment is generally obtained within one to two hours. In the alternative, cultured endothelial cells are added to the factor XIII/fibrinogen solution, thus trapping them within the coating. The coated material is then incubated to allow the cells to reproduce.

Within one embodiment of the invention, additional proteins are added to the fibrin coating to enhance endothelial cell attachment and/or chemotaxis. Proteins suitable in this regard include growth factors such as basic fibroblast growth factor (basic FGF) and endothelial cell growth factor (vascular endothelial cell growth factor), $α_2$ macroglobulin, vitronectin, fibronectin, and fibronectin fragments containing binding determinants for endothelial cells. Preparation of these proteins and protein fragments is within the level of ordinary skill in the art. See, for example, Gospodarowicz et al., U.S. Pat. Nos. 4,785,079 and 4,902,782; Obara et al., *FEBS Lett.* 213: 261–264, 1987; Dufour et al., *EMBO J.* 7: 2661–2671, 1988; Tischer et al., WO 91/02058; Boel et al., *Biochemistry* 29: 4081–4087, 1990; Ruoslahti et al., U.S. Pat. No. 4,614,517; Pierschbacher et al., U.S. Pat. No. 4,589,881; and Suzuki et al., *EMBO J.* 2519–2524, 1985, which are incorporated herein by reference. These proteins will generally be included in the fibrinogen/factor XIII solution at concentrations between about 0.5 and 10 µg/mL.

Fibrinogen is prepared according to known procedures, such as that of Straughn et al., *Thromb. Diath. Haemorrhag.* 16: 198, 1966, using sequential β-alanine precipitation. Further purification is obtained using DEAE-cellulose chromatography (Lawrie et al., *Biochem. Soc. Trans.* 7: 693-694, 1979). Autologous fibrinogen, which may further contain factor XIII and fibronectin, may be prepared as disclosed in U.S. Pat. Nos. 4,298,598 and 4,627,879.

Factor XIII for use within the present invention may be prepared from plasma according to known methods, such as those disclosed by Cooke and Holbrook (*Biochem. J.* 141: 79-84, 1974) and Curtis and Lorand (*Methods Enzymol.* 45: 177-191, 1976), incorporated herein by reference. The $a_2$ dimer form of factor XIII may be prepared from placenta as disclosed in U.S. Pat. Nos. 3,904,751; 3,931,399; 4,597,899 and 4,285,933, incorporated herein by reference. It is preferred, however, to use recombinant factor XIII so as to avoid to the use of blood- or tissue-derived products that carry a risk of disease transmission and avoid contamination with other proteins.

Methods for preparing recombinant factor XIII are known in the art. See, for example, Davie et al., EP 268,772 and Grundmann et al., AU-A-69896/87, which are incorporated herein by reference in their entirety. Within a preferred embodiment, the factor XIII $a_2$ dimer is prepared cytoplasmically in the yeast *Saccharomyces cerevisiae*. The cells are harvested and lysed, and a cleared lysate is prepared. The lysate is fractionated by anion exchange chromatography at neutral to slightly alkaline pH using a column of derivatized agarose, such as DEAE FAST-FLOW SEPHAROSE ™ (Pharmacia) or the like. Factor XIII is then precipitated from the column eluate by concentrating the eluate and adjusting the pH to 5.2-5.5, such as by diafiltration against ammonium succinate buffer. The precipitate is then dissolved and further purified using conventional chromatographic techniques, such as gel filtration and hydrophobic interaction chromatography.

Although it is preferred to use the factor XIII $a_2$ dimer within the present invention, other zymogen forms of factor XIII (e.g. $a_2b_2$ tetramer) may be used. Zymogen factor XIII is activated by thrombin present on the fibrin surface. However, activated factor XIII (factor XIIIa) may also be used.

Proteins for use within the present invention (including thrombin, fibrinogen and factor XIII) can be obtained from a variety of mammalian sources, such as human, bovine, porcine and ovine. As will be appreciated by those skilled in the art, in prosthetic applications it is preferred to use proteins syngeneic with the patient in order to reduce the risk of inducing an immune response. Non-human proteins are particularly useful in the preparation of materials for veterinary use or for use in experimental models.

The methods of the present invention are useful in the production of vascular grafts, artificial heart valves, cardiac assist devices and other prosthetic devices that are exposed to blood flow. Surfaces of such devices are prepared as disclosed herein, and the devices are implanted according to standard surgical techniques. In addition, the fibrinogen-coated polymer surfaces of the present invention provide a useful in vitro model for studying fibrin accretion, platelet adhesion and other phenomena related to vascular graft failure, as well as for testing of potential anti-thrombotic agents.

The following examples are offered by way of illustration, not limitation.

EXAMPLE 1

Polyethylene tubing (INTRAMEDIC PE 240, internal diameter 0.17 cm and INTRAMEDIC PE 320, internal diameter 0.27 cm, Clay Adams, Parsippany, N.J.) was cleaned with methanol and rinsed with distilled deionized water. The tubes were incubated overnight in TBS (0.05M Tris pH 7.4, 0.1M NaCl). The tubes were cut into 24-cm lengths.

The tubes were then coated with human fibrinogen (Grade L, Kabi Vitrum, Stockholm, Sweden). The fibrinogen was dialyzed against TBS and further purified by DEAE-cellulose chromatography essentially as described by Lawrie et al. (*Biochem. Soc. Trans.* 7: 693-694, 1979). The purified material was >96% thrombin-clottable. The tubes were filled with varying concentrations of fibrinogen in TBS. The solutions contained 1% of the fibrinogen as $^{125}$I-labeled protein (labeled by the solid phase lactoperoxidase-glucose oxidase procedure using Enzymobead reagent, Bio-Rad Ltd., Mississauga, Ontario, according to the directions of the supplier). The tubes were placed in an oven at 70° C. for 10 minutes, then extensively washed with distilled water to remove unbound fibrinogen. The quantity of bound fibrinogen was then determined by counting the radioactivity in the tubes. As shown in FIG. 1, the surface concentration of fibrinogen was directly dependent on the concentration of the fibrinogen solution.

To compare protein adsorption onto tubes coated with denatured fibrinogen with that onto uncoated tubes, pieces of tubing were exposed to solutions containing varying concentrations of $^{125}$I-labeled fibrinogen and human thrombin (Sigma), and $^{131}$I-labeled bovine albumin (Boehringer Mannheim Canada), all labeled using Enzymobead reagent (Bio-Rad Ltd.). The tubes were incubated with fibrinogen or albumin for 3 hours at 23° C., or with thrombin for 15 minutes at 23° C. The tubes were then rinsed three times with TBS, each wash consisting of 20 tube volumes drawn slowly through the tube. The radioactivity associated with the tubes was then measured. Adsorption of both fibrinogen and albumin to the thermally denatured fibrinogen surface was much less than to uncoated polyethylene.

Platelet adhesion to thermally-denatured fibrinogen (TDF) was then assessed. Suspensions of washed rabbit platelets were prepared according to the method of Ardlie et al. (*Br. J. Haemat.* 19: 7-17, 1970; *Proc. Soc. Exp. Biol. Med.* 136: 1021-1023, 1971) and labeled with Na$_2^{51}$CrO$_4$ (Du Pont-New England Nuclear, Boston, Mass., 200-500 mCi per mg chromium) for 30 minutes in the first washing solution. The platelets were then washed once in calcium-free Tyrode solution (136 mM NaCl, 0.1% glucose, 1 mM MgCl$_2$, 2 mM CaCl$_2$, buffered to pH 7.35 with NaHCO$_3$ and NaH$_2$PO$_4$) containing 4% albumin and resuspended at 500,000/μL in Eagle's medium containing 4% albumin, apyrase and 5 mM HEPES buffer (pH 7.35). Just prior to measurement of platelet adhesion, washed red blood cells were packed by centrifugation and added to the platelet suspension to obtain a 40% hematocrit (Cazenave et al., *J. Lab. Clin. Med.* 93: 60-70, 1979). The platelet:red cell suspensions were circulated for 10 minutes at 37° C. through polyethylene tubing (PE 240) which was either uncoated, coated with thermally-denatured fibrinogen (1 mg/mL in TBS) or coated with adsorbed nondenatured fibrinogen mg/mL in TBS, 3 hours, 22° C.). Flow was maintained at rates of either 2.5 mL/min. or 15 mL/min. using a variable-speed peristaltic pump. These flow rates correspond to wall shear rates of 90 sec$^{-1}$ and 550 sec$^{-1}$, respectively, under conditions of fully developed laminar flow. After washing the tubes with modified Tyrode solution (calcium omitted) containing 0.01M EDTA and 0.1% glucose, they were cut into 2-cm segments and counted for radioactivity.

Figure 2:
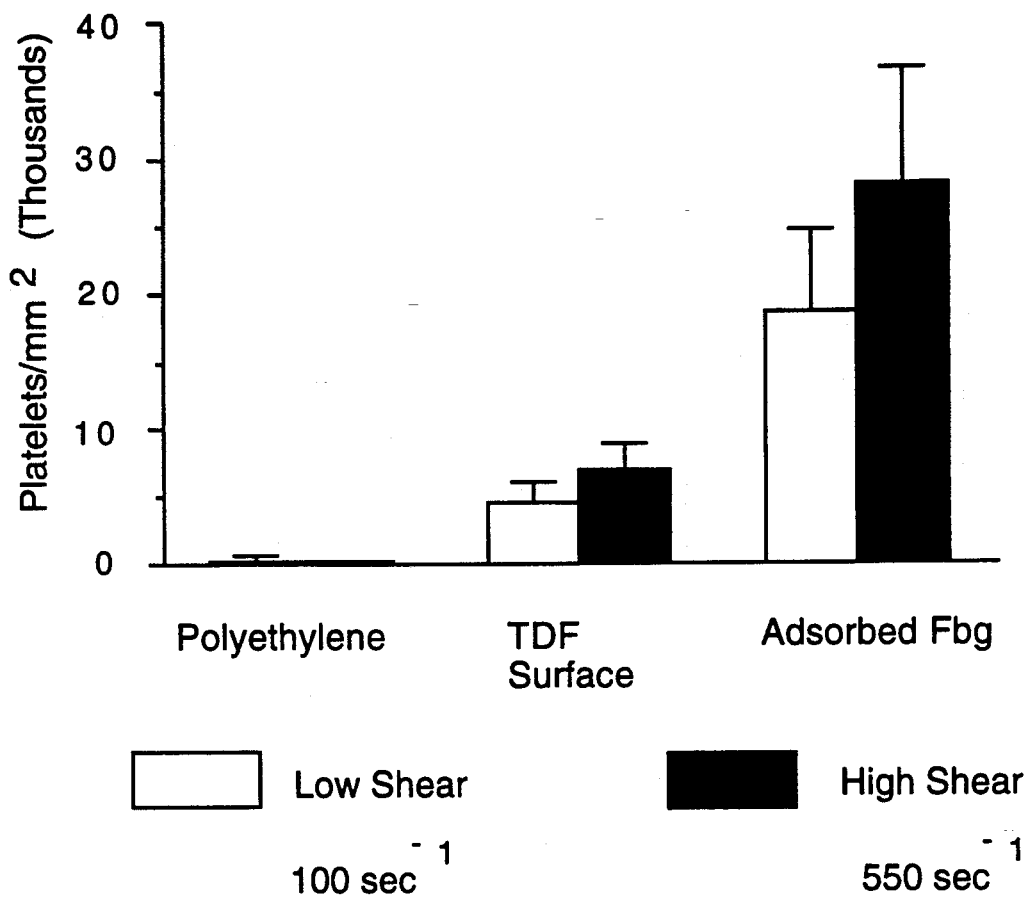
FIG. 2 illustrates platelet adhesion to uncoated polyethylene and polyethylene coated with thermally-denatured fibrinogen or adsorbed fibrinogen.

Platelet adhesion under low (90 sec$^{-1}$) and high (550 sec$^{-1}$) wall shear rates is illustrated in FIG. 2. There was a significant decrease, at both shear rates, in the platelet adhesion to the thermally-denatured fibrinogen compared to the adsorbed fibrinogen (p<0.01). Platelet adhesion to the uncoated polyethylene was undetectable.

To assess the stability of thermally-denatured fibrinogen to elution, PE 320 tubing was coated with thermally-denatured fibrinogen using a 1 mg/mL fibrinogen solution to which a radiolabeled fibrinogen tracer had been added. The tubing was then perfused for 24 hours with TBS at 37° C. and a flow rate of 20 mL/min. Four-cm segments were removed at hourly intervals to assess the stability of the fibrinogen layer under these flow conditions. In some experiments, pooled human plasma was used as the perfusate, at low and high flow rates (20 and 100 mL/min.) at 37° C. for 2 hours. Four-cm segments were removed at 5, 10, 15, 60 and 120 minutes to assess the stability of the fibrinogen layer in the presence of plasma.

There was no significant decrease in the radioactivity associated with the TDF surface when it was exposed to flowing TBS at 20 mL/minute for a period of 4 hours. Similarly, when perfusion was continued for 24 hours, there was also no decrease in the amount of fibrinogen in the layer (data not shown). Exposure of thermally-denatured fibrinogen-coated polyethylene to citrated human plasma at both low and high wall shear rates did not decrease the surface radioactivity over a 2 hour period (data not shown), indicating that the surface coating is stable and resists desorption even under conditions of flow.

EXAMPLE 2

Polyethylene tubing (INTRAMEDIC PE 240, Clay Adams) is rinsed with methanol followed by TBS and incubated overnight in TBS at room temperature. The tubing is then drained and filled with a solution of purified fibrinogen (1 mg/mL) in TBS. The tubing is placed in a 70° C. oven for ten minutes to denature the fibrinogen. The tubing is removed from the oven and rinsed with forty tube volumes of TBS.

The coated tubing is then treated with thrombin. The tubing is filled with a 1 µg/mL solution of human α-thrombin (Sigma Chemical Co., St. Louis, Mo.) in 0.5× TBS (hypotonic TBS). The tubes are incubated at room temperature for five minutes, then rinsed with twenty tube volumes of hypotonic TBS.

An additional layer of fibrin is then crosslinked to the coating. The thrombin-treated tubing is incubated for five minutes at 37° C. in a solution of 1 mg/ml fibrinogen and varying concentrations (0-5 µg/ml) recombinant factor XIII in TBS containing 2 mM CaCl$_2$. The tubing is then rinsed with TBS.

Figure 3:
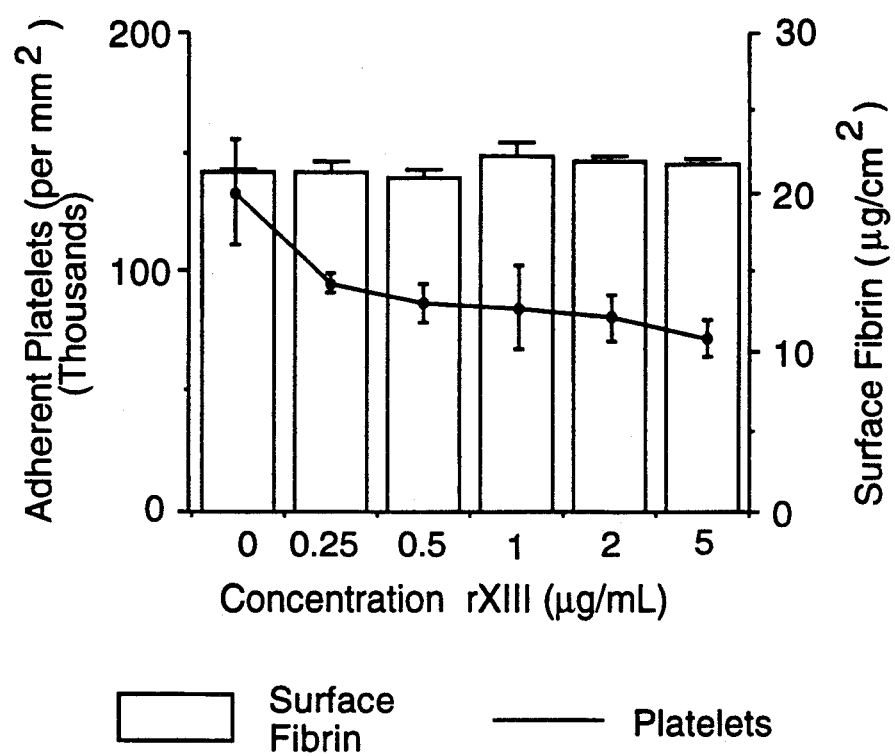
FIG. 3 illustrates the adhesion of platelets to fibrin coatings prepared using increasing amounts of factor XIII.

Platelet adhesion to tubing prepared in this way was assessed. $^{51}$Cr-labeled platelet: RBC suspensions were circulated through the tubing as described in Example 1. As shown in FIG. 3, platelet adhesion decreased with increasing amounts of factor XIII.

EXAMPLE 3

Fibrin-coated polyethylene was used to compare the effectiveness of heparin and the antithrombin III-independent thrombin inhibitors hirudin, Hirulog-1 and D-phenylalanyl-L-prolyl-L-arginyl chloromethyl ketone (PPACK) in inhibiting fibrin accretion from plasma devoid of the vitamin K-dependent coagulation factors onto a fibrin-thrombin surface. All solutions were prepared in TBS except as noted. Standard heparin from porcine intestinal mucosa (grade II) was obtained from Sigma Chemical Co., St. Louis, Mo., and PPACK was obtained from Calbiochem Corp., San Diego, Calif. PPACK was prepared in 10$^{-3}$M HCl. Recombinant hirudin was a gift of Dr. H. Grossenbacher, Ciba-Geigy Ltd., Biotechnology Department, Basel, Switzerland (Lot rHH5-7033/#A19). This molecule is a single-chain polyepeptide of 65 amino acids with three disulfide bridges. It has the same amino acid sequence and structure as native hirudin, variant HV-1. Hirulog-1, a synthetic hirudin derivative, was a gift of Dr. John Maraganore, Biogen Inc., Cambridge, Mass. Recombinant hirudin and Hirulog-1 were prepared in TBS containing 6 mg/mL polyethylene glycol 8000 (PEG 8000) to avoid wall effects (Degryse et al., *Thromb. Res.* 61: 87, 1991).

Whole blood, collected in acid-citrate dextrose from 15 healthy donors, was obtained from the Canadian Red Cross. The cellular components were removed by centrifugation, and the vitamin K-dependent clotting factors were removed by the addition of 100 mL of 1M BaCl$_2$ per liter of plasma. After gentle stirring for 1 hour at 4° C., the insoluble barium citrate was removed by centrifugation, and the supernatant plasma was dialyzed overnight against 0.15M NaCl. HEPES buffer was added to a final concentration of 50 mM and the pH was adjusted to 7.4. The plasma was stored at −70° C. The fibrinogen concentration, as determined by the measurement of clottable protein (Ratnoff et al., *J. Lab. Clin. Med.* 37: 316, 1951), was 2.2 mg/mL. The ATIII and heparin cofactor II (HCII) levels were measured on an Automated Coagulation Laboratory (ACL 300, Instrumentation Laboratory, Milan, Italy) according to instructions from the supplier (Diagnostica Stago., Asnieres, France) and were found to be 0.98 U/mL and 0.67 U/mL, respectively. Plasma prothrombin, determined using rabbit brain thromboplastin and factor II-deficient plasma (Owren, *J. Clin. Lab. Invest.* 1: 81, 1949), was less than 0.01 U/mL. The addition of CaCl$_2$ to this plasma (final concentration, 2 mM) did not result in clot formation when it was left overnight at 37° C.

Polyethylene tubing (Intramedic PE 240, Clay Adams) was coated with fibrinogen (purified from citrated human plasma using sequential β-alanine precipitation as disclosed by Straughn and Wagner, *Thromb. Diath. Haemorrhag.* 16: 198, 1966). The tubing was first washed with methanol and TBS, then filled with TBS containing 1 mg/mL fibrinogen and heated to 70° C. for 10 minutes. The tubing was then washed with 50 tube volumes of TBS. The tubes were drained and filled with a solution containing 1 µg/mL human α-thrombin (obtained from Dr. J. Fenton II, New York State Department of Health, Albany, N.Y.) in hypotonic TBS. After incubation for five minutes at room temperature, the tubes were washed with 10 tube volumes of hypotonic TBS, then with 10 tube volumes of TBS containing 1 mg/mL human fibrinogen and 2 mM CaCl$_2$. The tubes were incubated at 37° C. for 10 minutes, then washed with 100 tube volumes of 0.05M $Na_2HPO_4$, pH 6.5.

The quantity and uniformity of the resulting fibrin-thrombin surface was assessed by using radiolabeled tracer proteins ($^{125}$I-thrombin, $^{131}$I-fibrinogen) in both of the solutions used to prepare the surface. The amounts of fibrin and thrombin bound to the surface was determined by measuring the radioactivity of equivalent sized segments cut from the tubing in a gamma counter MINAKI gamma. AUTO-gamma 5000 series, Canberra-Packard Canada, Ltd., Mississauga, Ont.). The variation in the amount of fibrin and thrombin on the surfaces was less than 10% between the segments tested.

To further assess the uniformity and the morphologic characteristics of the fibrin-coated surface, segments were fixed in 4% paraformaldehyde followed by 1% osmium tetroxide in 0.1M sodium cacodylate buffer, dehydrated through graded ethanol, and dried in a $CO_2$ critical-point dryer (Bomar SPC-900). The tubes were then mounted on aluminum specimen stubs, sputter-coated with gold and examined in a Philips 501-B scanning electron microscope at low (40×) and high (2500×) power. There was a uniform thin layer of polymerized fibrin adherent along the length of the luminal aspect of the tubing. The surface area to weight ratio of the fibrin on the surface was calculated to be 67 $cm^2$/mg fibrin.

Segments of fibrin-coated tubes were divided lengthwise and boiled in a solution containing 8M urea, 2% sodium dodecyl sulfate (SDS), 100 mM $\beta$-mercaptoethanol for 1 hour at 100° C. Analysis of the digested surface material using SDS-PAGE (Laemmli, *Nature* 227: 680, 1970) showed that this material contained gamma-gamma dimers consistent with the presence of cross-linked polymerized fibrin.

The equivalent anti-thrombin concentrations of the study anticoagulants was determined using a modification of the methods of Hatton (*Biochem. J.* 131: 799, 1973). In a 12×85 mm borosilicate glass tube, 200 $\mu$l of Ringers Lactate and 100 $\mu$l of the test plasma were incubated at 37° C. for 3 minutes, then 100 $\mu$l of chilled TBS containing human $\alpha$-thrombin was added. The clotting time was determined using the tilt-tube method. The amount of thrombin added was calculated to give a baseline thrombin clotting time of 20 seconds. The test anticoagulants were then added to the plasma at varying concentrations and the clotting time test was repeated with identical amounts of added thrombin. By plotting the concentration of the anti-coagulant against the log of the clotting time, extrapolation to equivalent anti-thrombin concentrations that prolong clot tilt test 2 ×baseline (40 sec.) could be made for each of the drugs. The recorded observations were based on the average of 4 readings taken on 2 separate days.

Inhibition of thrombin by Hirulog-1 was also assessed by incubating human $\alpha$-thrombin (42 nM, 1.5 $\mu$g/mL) with Hirulog-1 (42 nM, 0.12 $\mu$g/mL and 420 nM, 1.2 $\mu$g/mL) in TBS with 6 mg/mL PEG 8000 (37° C.). Aliquots of the incubate (100 $\mu$L) were taken at varying time intervals and were added to plasma to determine the clotting time as described above.

The equivalent anti-thrombin concentrations of the study anticoagulants that prolonged the clot time of the test plasma from a baseline of 20 seconds to 40 seconds were: recombinant hirudin, 25 nM (0.17 $\mu$g/mL); Hirulog-1, 42 nM (0.12 $\mu$g/mL); PPACK, 65 nM; heparin, 0.23 U/mL.

PE tubes (6 cm) coated with fibrin-thrombin, were washed with 1 mL of plasma prepared as described above. The plasma contained the test anticoagulants in varying concentrations, $^{125}$I-labeled fibrinogen (labeled by the solid-phase lactoperoxidase-glucose oxidase procedure) as a tracer protein, and 2 mM $CaCl_2$. The tubes were incubated at 37° C. for varying time intervals, and then perfused with TBS on a roller pump (Harvard Apparatus Variable Speed Peristaltic Pump, Harvard Apparatus Inc., South Natick, Mass.) at 10 mL/min. for 10 minutes (shear rate 365 $sec^{-1}$) at 37° C. The end 1-cm segments were discarded, and the radioactivity of the remaining tubing was measured in order determine the amount of accreted fibrin.

The surface $^{125}$I-labeled fibrin which accreted on the PE tubes from test plasma (30 min. incubation, 37° C.) in the presence and absence of Hirulog-1 (42 nm) was digested in 1 mL 8M urea, 2% SDS, 100 mM $\beta$-mercaptoethanol for 1 hour at 100° C. Equal volumes of the digested material were assessed by gel electrophoresis on SDS-polyacrylamide. After drying the gel, it was exposed to Kodak X-AR5 film, and the bands which formed were assessed densitometrically using an LKB ULTRASCAN XL Laser Densitometer (Pharmacia LKB Biotechnology, Uppsala, Sweden).

Figure 4:
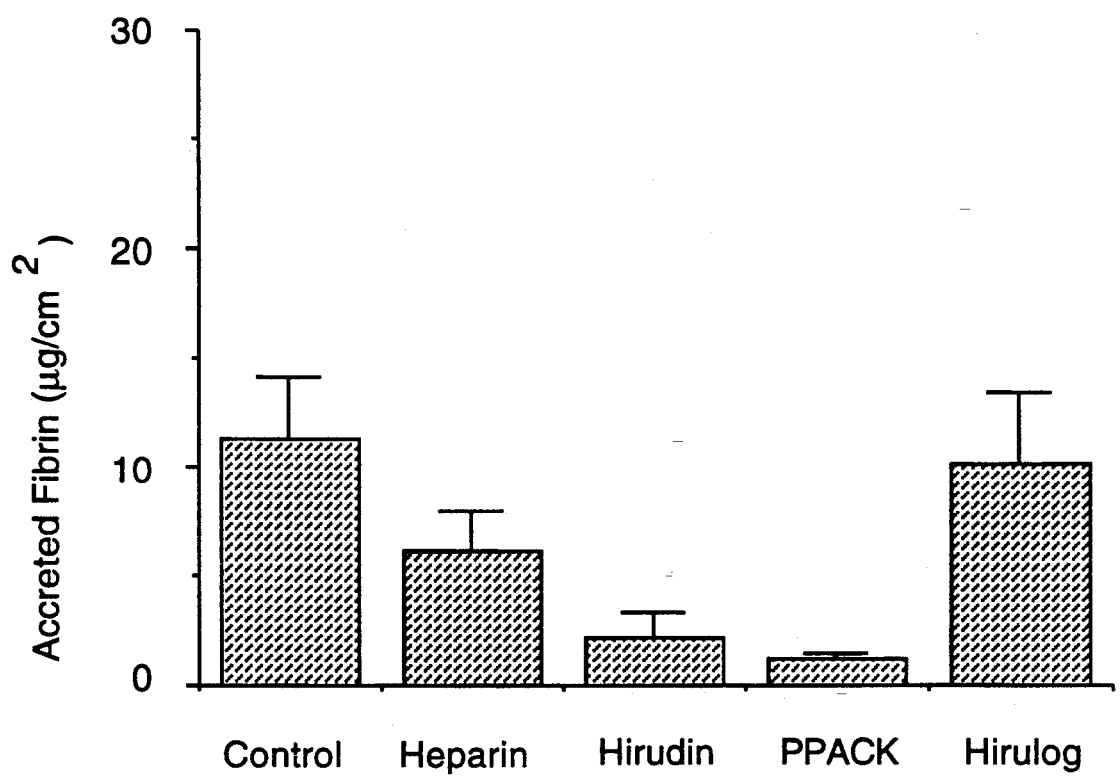
FIG. 4 illustrates the inhibition of fibrin accretion by various anticoagulants in a ten minute assay.

As illustrated in FIG. 4, after 10 minutes of incubation of the test plasma with the fibrin-coated PE tubing, all of the anticoagulants were able to inhibit fibrin accretion as compared to the control plasma, except for Hirulog-1. Both recombinant hirudin and PPACK were significantly more effective than either control ($p<0.001$, Student's t-test), Hirulog-1 ($p<0.001$) or heparin ($p<0.001$) in inhibiting fibrin accretion. There was no significant difference between the inhibition of fibrin accretion by the anticoagulants recombinant hirudin and PPACK.

Figure 5:
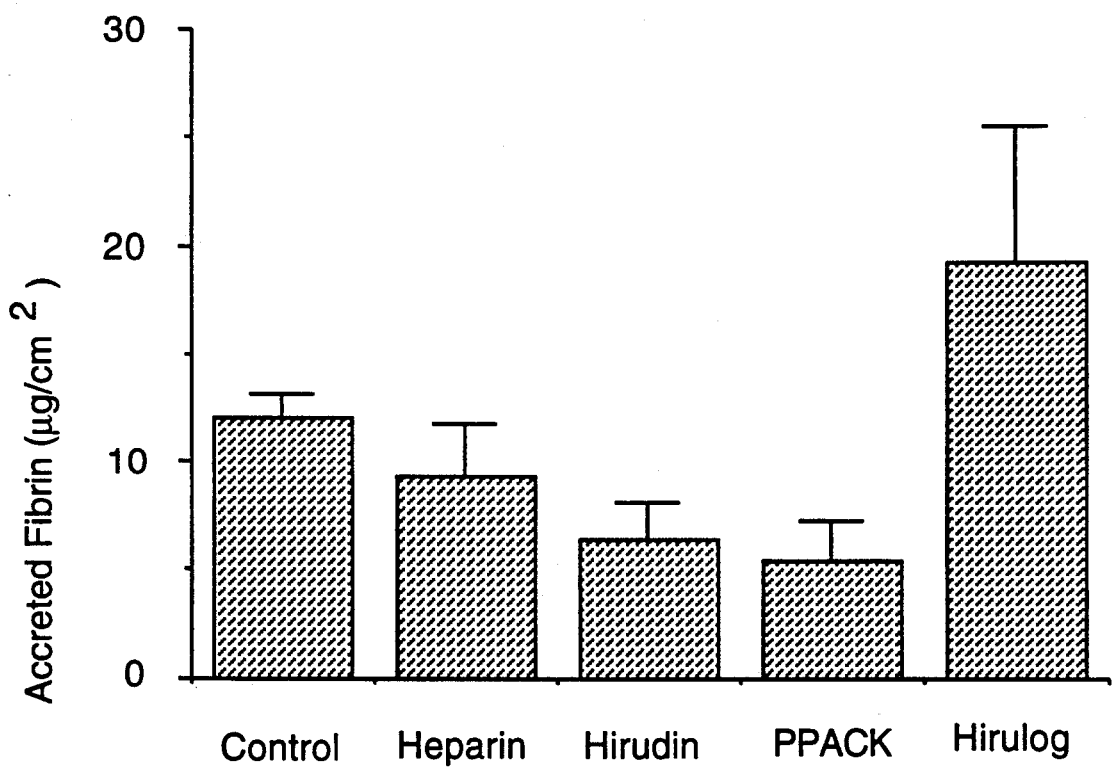
FIG. 5 illustrates the inhibition of fibrin accretion by various anticoagulants in a thirty minute assay.

At 30 minutes of incubation (FIG. 5) the degree of inhibition of fibrin accretion of the fibrin-coated tubes by the anticoagulants was less than at 10 minutes. Both recombinant hirudin and PPACK reduced accretion compared to control ($p<0.001$), but heparin did not ($p<0.02$). Further, there was an increase in the amount of fibrin accreted on the fibrin-thrombin surface in the presence of the anticoagulant Hirulog-1 as compared to the control plasma ($p<0.02$).

Figure 6:
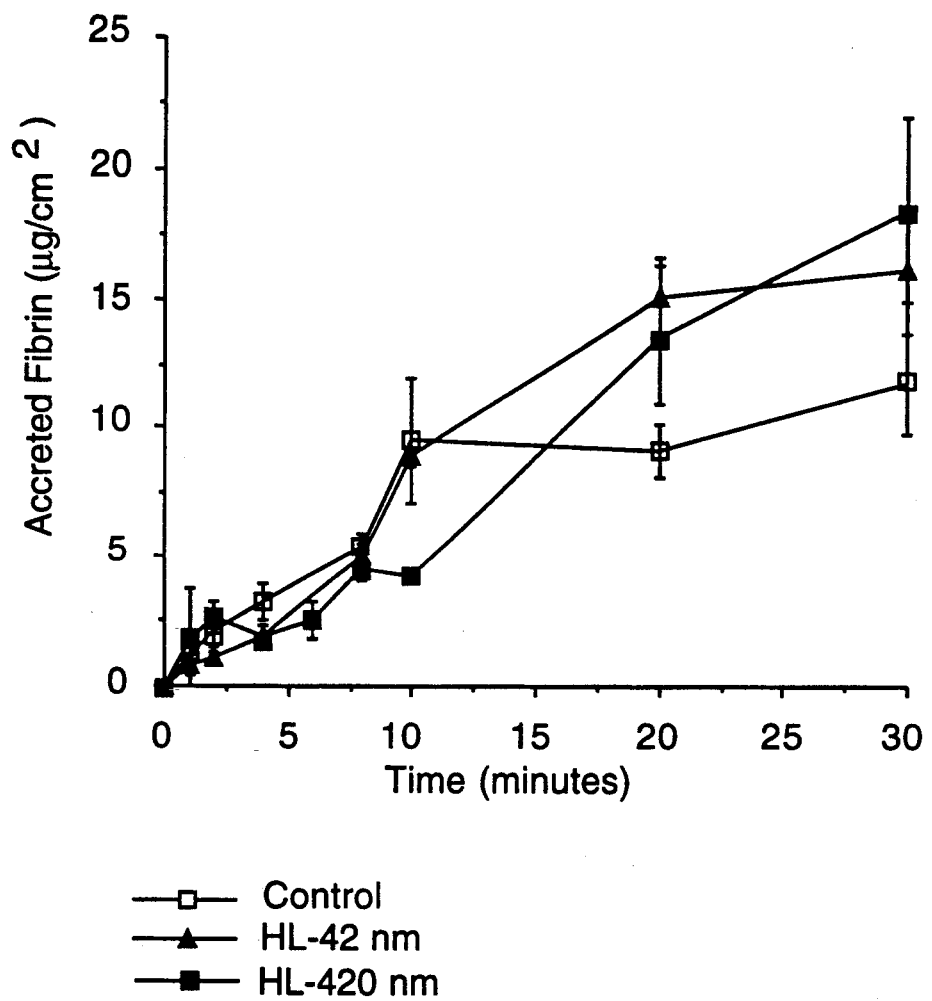
FIG. 6 illustrates the effect of a synthetic hirudin derivative on fibrin accretion on fibrin-coated polyethylene.

In a separate experiment in which fibrin accretion on fibrin-thrombin coated PE tubes was assessed in the presence and absence of Hirulog-1 (FIG. 6), low concentrations of Hirulog-1 (42 nM) inhibited fibrin accretion for 4 minutes and high concentrations (420 nM) inhibited fibrin accretion for 8 minutes, as compared to control. These concentrations represented a 3- and 30-fold molar excess of Hirulog-1 relative to the amount of $\alpha$-thrombin bound to the fibrin-coated surface (3.2 ng thrombin/$cm^2$, 15 nM/$cm^2$). After those time points however, there was a progressive increase in the amount fibrin accreted at both concentrations of Hirulog-1 in plasma as compared to control plasma (30 min. incubation Hirulog-1; 18.4±3.5 $\mu$g fibrin/$cm^2$, Control; 11.7±2.0 $\mu$g fibrin/$cm^2$, $p<0.001$). SDS-PAGE and autoradiography with densitometric analysis of the radiolabeled accreted fibrin which had been digested (8M urea, 2% SDS, 100 mM $\beta$-mercaptoethanol, 1 hour, 100° C.) confirmed that the amount accreted in the presence of Hirulog-1 was increased and that the fibrin contained gamma-gamma dimers consistent with accreted polymerized cross-linked fibrin and not adsorbed fibrinogen (ratio gamma-gamma peak Hirulog-1:Control; 1.3).

Figure 7:
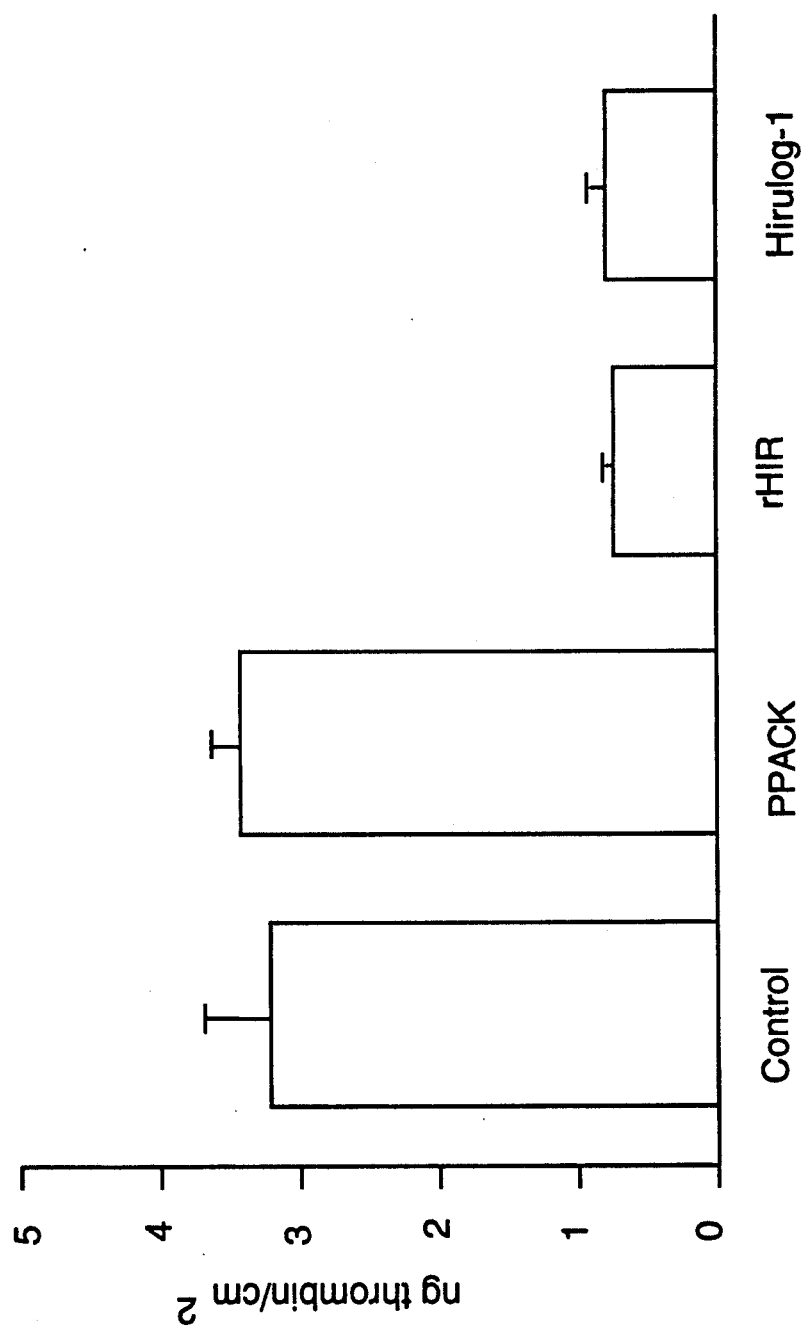
FIG. 7 illustrates the results of an assay of thrombin displacement using fibrin-coated polyethylene.

Fibrin coated PE tubing was prepared as described above using $^{125}$I-thrombin (labeled by the solid phase lactoperoxidase-glucose oxidase procedure). The tubing was then rinsed with TBS containing the ATIII-independent thrombin inhibitors at concentrations 5 times that required to prolong the clot tilt test 2 times baseline. After an incubation period of 10 minutes (23° C.), the tubes were rinsed with hypotonic TBS on a roller pump (10 mL/min., 10 min.). The radioactivity associated with each tube was measured to determine the amount of surface thrombin remaining. FIG. 7 shows the effect of the ATIII-independent thrombin inhibitors on displacement of thrombin from the fibrin surface. Whereas PPACK did not cause any displacement, both recombinant hirudin and Hirulog-1 significantly decreased the surface concentration of the thrombin bound to the polymerized fibrin as compared to the control buffer ($p<0.001$).

Although certain embodiments of the invention have been described in detail for purposes of illustration, it will be readily apparent to those skilled in the art that the methods and compositions described herein may be modified without deviating from the spirit and scope of the invention. Accordingly, the invention is not limited except as by the appended claims.

We claim:

1. In a method of coating a surface of a polymeric material with fibrin, the improvement comprising:

incubating said polymeric material in a solution of fibrinogen at a temperature of at least 56° C. but less than 100° C. to produce a fibrinogen-coated surface;

treating the fibrinogen-coated surface with thrombin to produce fibrin monomers; and then exposing the thrombin-treated surface to a solution comprising factor XIII and additional fibrinogen, whereby the additional fibrinogen is converted to fibrin and cross-linked to the fibrin-coated surface.

2. A method according to claim 1 wherein the factor XIII concentration in the solution comprising factor XIII and additional fibrinogen is from 0.25–20 μg/mL.

3. A method according to claim 1 wherein the factor XIII concentration in the solution comprising factor XIII and additional fibrinogen is from 0.25–5.0 μg/mL.

4. A method according to claim 1 wherein the fibrinogen concentration in the solution comprising factor XIII and additional fibrinogen is from 0.5–5.0 mg/mL.

5. A method according to claim 1 wherein said solution comprising factor XIII and additional fibrinogen further comprises basic fibroblast growth factor, endothelial cell growth factor, $\alpha_2$ macroglobulin, vitronectin, fibronectin, or a cell-binding fragment of fibronectin.

6. A method according to claim 1 wherein said solution comprising factor XIII and additional fibrinogen comprises endothelial cells.

7. A method according to claim 1 further comprising the step of seeding the cross-linked fibrin with endothelial cells.

8. A polymeric material prepared according to the method of claim 1.

9. A polymeric material prepared according to the method of incubating said polymeric material in a solution of fibrinogen at a temperature of at least 56° C. but less than 100° C. to produce a fibrinogen-coated surface.

10. A polymeric material prepared according to the method of:

incubating said polymeric material in a solution of fibrinogen at a temperature of at least 56° C. but less than 100° C. to produce a fibrinogen-coated surface; and then treating the fibrinogen-coated surface with thrombin to produce fibrinogen monomers.

* * * * *